(12) United States Patent
Sugiura et al.

(10) Patent No.: US 8,232,416 B2
(45) Date of Patent: Jul. 31, 2012

(54) METHOD OF MANUFACTURING PERFLUORINATED POLYFUNCTIONAL VINYL ETHER COMPOUND

(75) Inventors: Hiroki Sugiura, Kanagawa (JP); Masayuki Harada, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 655 days.

(21) Appl. No.: 12/392,721

(22) Filed: Feb. 25, 2009

(65) Prior Publication Data

US 2009/0216030 A1    Aug. 27, 2009

(30) Foreign Application Priority Data

Feb. 26, 2008   (JP) .................. 2008-044788

(51) Int. Cl.
*C07D 319/00*   (2006.01)
*C07C 65/00*    (2006.01)
*C07C 51/58*    (2006.01)

(52) U.S. Cl. ......... 549/335; 562/863; 562/852; 562/474
(58) Field of Classification Search .................. 549/335; 562/863, 852, 474
See application file for complete search history.

(56) References Cited

U.S. PATENT DOCUMENTS

| | | | |
|---|---|---|---|
| 5,756,814 A | 5/1998 | Lin | |
| 6,586,626 B2 | 7/2003 | Okazoe | |
| 6,833,477 B2 | 12/2004 | Okazoe et al. | |
| 6,951,957 B2 | 10/2005 | Okazoe | |
| 7,071,272 B2 | 7/2006 | Okazoe | |
| 7,083,705 B2 | 8/2006 | Okazoe | |

FOREIGN PATENT DOCUMENTS

| | | |
|---|---|---|
| JP | 64-3140 A | 1/1989 |
| JP | 2001-139509 A | 5/2001 |
| JP | 2004-18424 A | 1/2004 |
| JP | 3882229 B2 | 11/2006 |
| WO | 02/26682 A1 | 4/2002 |
| WO | 02/26687 A1 | 4/2002 |

*Primary Examiner* — Noble Jarrell
*Assistant Examiner* — Raymond Covington
(74) *Attorney, Agent, or Firm* — Sughrue Mion, PLLC

(57) ABSTRACT

A method of manufacturing a compound represented by formula (2) is provided, the method including thermally decomposing a compound represented by formula (1) under a reduced pressure:

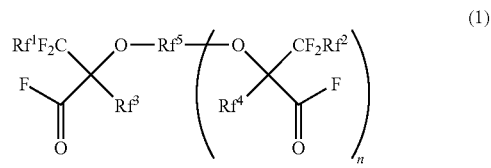

(1)

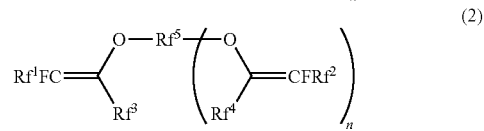

(2)

wherein $Rf^1$ and $Rf^2$ each independently represents a fluorine atom or a perfluorinated monovalent substituent, $Rf^3$ and $Rf^4$ each independently represents a fluorine atom, a perfluorinated monovalent substituent or a perfluorinated divalent substituent, $Rf^3$ and $Rf^4$ may combine with each other to form a ring, each of $Rf^3$ and $Rf^4$ may combine with $Rf^5$ to form a ring, and $Rf^5$ represents a perfluorinated (n+1)-valent to (2n+2)-valent linkage group, provided that n represents an integer of 1 to 5.

8 Claims, No Drawings

METHOD OF MANUFACTURING PERFLUORINATED POLYFUNCTIONAL VINYL ETHER COMPOUND

BACKGROUND OF THE INVENTION

1. Field of the Invention

The present invention relates to a method of manufacturing a perfluorinated polyfunctional vinyl ether compound.

2. Description of the Related Art

Fluorine-containing polymers each have many excellent properties, such as water- and oil-repellent properties, heat resistance, chemical resistance and having a low refractive index, and are used in a wide variety of fields, such as those of coating agents (as described, e.g., in JP-A-2006-38438), seal members (as described, e.g., in JP-A-2007-146096) and cosmetics (as described, e.g., in JP-A-2007-269642).

Among them, a perfluorinated vinyl ether compound having a perfluorinated vinyl ether group ($-OCF=CF_2$) is one of monomers most frequently used as raw materials of fluoropolymers. A known method for manufacturing a perfluorinated vinyl ether compound on an industrial scale is decarboxylation by heating of a carboxylate containing a group $-OCF_2CF_2COOM$ or a group $-OCF(CF_3)COOM$ (wherein M represents a metal, e.g., an alkali metal) (as described, e.g., in JP-A-2004-18424). However, the decarboxylation is generally attended with difficulty in drying the carboxylate. And it is known that insufficient drying of the carboxylate gives rise to formation of the group $-OCHFCF_3$ as a by-product that comes from addition of hydrogen fluoride to the group $-OCF=CF_2$. Presence of the group $-OCHFCF_3$ in a compound having two or more perfluorinated vinyl ether groups is undesirable, because the group $-OCHFCF_3$ shows no ability to polymerize and becomes a cause of a drop in cross-linkage density in the case of manufacturing a polymer by polymerizing the perfluorinated vinyl ether groups. On the other hand, dechlorination from the group $-OCClFCClF_2$ by use of zinc (as described, e.g., in Japanese Patent No. 3,882,229) is known as another industrial method for manufacturing a perfluorinated vinyl ether compound without utilizing the decarboxylation. However, this dechlorination requires an additional operation for disposal of zinc chloride as a by-product, so it is at an economical disadvantage by incurring additional costs.

By contrast, the method of manufacturing a perfluorinated vinyl ether compound in a flow method allows continuous reaction, and is one of the most useful methods suited for industrial operations. The term "a flow method" as used herein refers to a process in which a compound having the group $-OCF(CF_3)COF$ or the group $-OCF_2CF_2COF$ (a raw material) is introduced into a tubular reactor heated to high temperatures, and subjected to thermal decomposition in its vapor phase, thereby converting the group therein into the group $-OCF=CF_2$. In the flow method, a granular filler such as glass beads is generally packed in a reactor to heighten thermal conductivity, and thereby reaction in the reactor is accelerated. And the duration of contact between a raw material and a filler in the flow method is one of important factors affecting a conversion ratio in the reaction. Therefore, for the purpose of controlling the duration of the contact, the reaction is carried out under normal atmospheric pressure while flowing an inert gas, such as nitrogen or helium, through the reactor. Moreover, the supply of an inert gas flow is important in not only drying the filler and inhibiting formation of the group $-OCHFCF_3$ as a by-product but also accelerating the vaporization of a raw material. Therefore, all of known flow methods are performed under normal atmospheric pressure. Such a flow method can provide the desired product in a high yield so long as the compound as a raw material has one group of the formula $-OCF(CF_3)COF$ or $-OCF_2CF_2COF$. However, when it is intended to derive a compound having more than one group of the formula $-OCF=CF_2$, namely a perfluorinated polyfunctional vinyl ether compound, from the compound having a plurality of those groups, there occurs a problem that the yield of the product is low and the productivity is bad. For instance, the yield of $FSO_2(CF_2)_2OCF(CF_2OCF=CF_2)_2$ stands at a low of 31.5% in the case of deriving such a compound from $FSO_2(CF_2)_2OCF(CF_2OCF(CF_3)COF)_2$ in accordance with a flow method(see JP-A-64-3140), so it cannot be said that the flow method has manufacturing suitability. In addition, the yield of $F_2C=FCOCF=CF_2$ stands at a low of 41% in the case of deriving such a compound from $FCO(CF_2)_2OCF(CF_3)COF$ in accordance with a flow method, so it is also hard to say that the flow method has manufacturing suitability.

On the other hand, where the conduct of a flow method under a reduced pressure is concerned, there are some specifications (see JP-A-2001-139509, WO 02/026682, brochure and WO 02/026687, brochure) having such a description that, when a substrate used has a high boiling point, it is advisable to conduct reaction under a reduced pressure. However, there has been no reported case of putting vapor-phase thermal decomposition reaction under a reduced pressure into practice. In addition, no description about relationship between the number of functional groups in an acid fluoride and the reaction pressure has been found, and no attempt to manufacture a perfluorinated polyfunctional vinyl ether compound(s) in a flow method under a reduced pressure has been made at all.

SUMMARY OF THE INVENTION

The invention brings a resolution to a problem that thermal decomposition of a perfluorinated polyfunctional vinyl ether compound by a flow method is low in yield and deficient in suitability as a manufacturing method. And the invention aims to provide a method of manufacturing a perfluorinated polyfunctional vinyl ether compound useful as a raw material of fluoropolymers at a high yield and a high purity in accordance with a reduced-pressure flow method.

A cause of the problem that thermal decomposition of a perfluorinated polyfunctional vinyl ether compound by the flow method currently in use is low in yield and deficient in suitability as a manufacturing method is supposed to be ascribed to formation of a greater quantity of decomposed matter from the product by side reaction, such as polymerization reaction of vinyl group, as compared with the case of a perfluorinated monofunctional vinyl ether compound, because of the presence of a plurality of highly-reactive perfluorinated vinyl ether groups in the perfluorinated polyfunctional vinyl ether compound. As a result of our intensive study, we have conceived that, when performance of a flow method under a reduced pressure can prevent product decomposition from occurring and ensure manufacturing of a perfluorinated polyfunctional vinyl ether compound in a high yield, it will become an extremely useful method for manufacturing such a compound on an industrial scale, thereby attaining the invention.

That is, solutions to the problem are attained by the following manufacturing methods:

(1) A method of manufacturing a compound represented by formula (2), the method comprising:

thermally decomposing a compound represented by formula (1) under a reduced pressure:

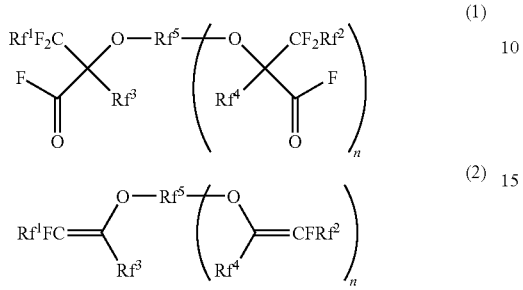

wherein $Rf^1$ and $Rf^2$ each independently represents a fluorine atom or a perfluorinated monovalent substituent;

$Rf^3$ and $Rf^4$ each independently represents a fluorine atom, a perfluorinated monovalent substituent or a perfluorinated divalent substituent;

$Rf^3$ and $Rf^4$ may combine with each other to form a ring;

each of $Rf^3$ and $Rf^4$ may combine with $Rf^5$ to form a ring; and $Rf^5$ represents a perfluorinated (n+1)-valent to (2n+2)-valent linkage group, provided that n represents an integer of 1 to 5.

(2) The manufacturing method as described in item (1), wherein the compound represented by formula (1) is thermally decomposed under an absolute pressure of 100 mmHg or below.

(3) The manufacturing method as described in item (1), wherein the compound represented by formula (1) is thermally decomposed under an absolute pressure of 50 mmHg or below.

(4) The manufacturing method as described in item (1), wherein the compound represented by formula (1) has a boiling point of 350° C. or below under an absolute pressure of 100 mmHg.

(5) The manufacturing method as described in any of items (1) to (4), wherein the compound represented by formula (1) is a compound represented by formula (3) and the compound represented by formula (2) is a compound represented by formula (4):

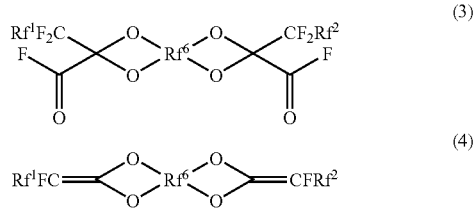

wherein $Rf^1$ and $Rf^2$ each independently represents a fluorine atom or a perfluorinated monovalent substituent; and $Rf^6$ represents a perfluorinated tetravalent linkage group.

(6) The manufacturing method as described in item (5), wherein the compound represented by formula (3) is a compound represented by formula (5) and the compound represented by formula (4) is a compound represented by formula (6):

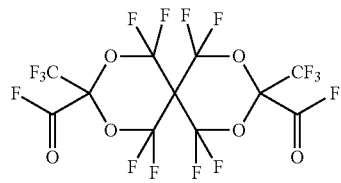

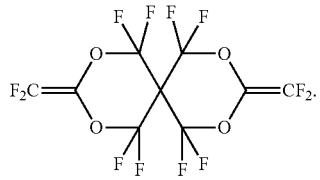

DETAILED DESCRIPTION OF THE INVENTION

A more detailed description of the invention is given below.

The term "perfluorinated" used in this specification refers to the state in which fluorine atoms are substituted for all the hydrogen atoms.

The term "a perfluorinated vinyl ether" used in this specification signifies a group represented by —OCF=CF₂ or a group —OCF=CF₂ in which 1 to 3 fluorine atoms out of 3 fluorine atoms are substituted. The term "a perfluorinated polyfunctional vinyl ether compound" signifies a perfluorinated compound having two or more perfluorinated vinyl ether groups.

Descriptions of substituents and linkage groups in the formulae (1) to (4) are given below.

It is preferable that none of $Rf^1$, $Rf^2$, $Rf^3$, $Rf^4$, $Rf^5$ and $Rf^6$ undergo changes by thermal decomposition reaction. The group resistive to change by thermal decomposition is a group free of a moiety represented by —COX. Herein, X represents a fluorine atom, a chlorine atom, a bromine atom, an iodine atom or a group represented by —OY (wherein Y represents an alkali metal atom, such as a lithium atom, a sodium atom, a potassium atom or a cesium atom).

The halogen in a halogenated alkyl group represented by $Rf^1$, $Rf^2$, $Rf^3$ and $Rf^4$ each, the halogen in a halogenated alkylene group represented by $Rf^3$ and $Rf^4$ each, and the halogen in a halogenated linkage group represented by $Rf^5$ and $Rf^6$ each are chlorine, bromine or iodine, preferably chlorine or bromine, and far preferably chlorine.

$Rf^1$ and $Rf^2$ each represent a fluorine atom or a perfluorinated monovalent substituent independently. The monovalent substituent to be perfluorinated may have any of linear, branched and cyclic structures, and the number of carbon atoms contained therein is preferably from 1 to 10, far preferably from 1 to 5, particularly preferably from 1 to 3. Examples of a monovalent substituent to be perfluorinated include an alkyl group (e.g., methyl, ethyl, n-propyl, i-propyl, cyclopropyl), a halogenated alkyl group (e.g., chloromethyl, dichloromethyl, trichloromethyl, 1-chloroethyl, 2-chloroethyl), an alkoxy group (e.g., methoxy, ethoxy, n-propoxy), an acyl group (e.g., formyl, acetyl, propionyl), an acyloxy group (e.g., acetoxy, propionyloxy), an alkoxycarbonyl group (e.g., methoxycarbonyl, ethoxycarbonyl), and a fluorosulfonyl group. Each of these monovalent substituents may further have another substituent.

Examples of $Rf^1$ and $Rf^2$ each include a fluorine atom, a trifluoromethyl group, a pentafluoroethyl group, heptafluoro-n-propyl group, heptafluoro-i-propyl group, a chlorodifluoromethyl group, a dichlorofluoromethyl group, a trichloromethyl group, a 1-chlorotetrafluoroethyl group, a 2-chlorotetrafluoroethyl group, a 1,1-dichlorotrifluoroethyl group, a 1,2-dichlorotrifluoroethyl group, a 2,2-dichlorotrifluoroethyl group, a 2,2,2-trichlorodifluoroethyl group, a 1,1,2-trichlorodifluoroethyl group, a 2,2,1-trichlorodifluoroethyl group, a 1,2,2,2-tetrachlorofluoroethyl group, a 1,1,2,2-tetrachlorofluoroethyl group, a pentachloroethyl group, a 1-chlorohexafluoro-n-propyl group, a 2-chlorohexafluoro-n-propyl group, a 3-chlorohexafluoro-n-propyl group, a 1-(chlorodifluoromethyl)tetrafluoroethyl group, a 1-(trifluoromethyl)-1-chlorotetrafluoroethyl group, a 1,1-dichloropentafluoro-n-propyl group, a 1,2-dichloropentafluoro-n-propyl group, a 1,3-dichloropentafluoro-n-propyl group, a 2,3-dichloropentafluoro-n-propyl group, a 2,2-dichloropentafluoro-n-propyl group, a 3,3-dichloropentafluoro-n-propyl group, a 1-(chlorodifluoromethyl)-2-chlorotrifluoroethyl group, a 1-(dichlorofluoromethyl)tetrafluoroethyl group, a trifluoromethoxy group, a pentafluoroethoxy group, a heptafluoro-n-propoxy group, a heptafluoro-i-propoxy group, a pentafluoromethoxymethyl group, a heptafluoroethoxymethyl group, a heptafluoromethoxyethyl group, a heptafluoro-1-methoxyethyl group, a trifluoroacetyl group, a pentafluoropropionyl group, a pentafluoroacetylmethyl group, a trifluoromethoxycarbonyl group, a pentafluoroethoxycarbonyl group, a pentafluoromethoxycaronylmethyl group, a trifluoroacetoxy group, a pentafluoroacetoxymethyl group, a pentafluoropropionyloxy group, a fluorosulfonyl group, a fluorosulfonyldifluoromethyl group, a fluorosulfonyltetrafluoroethyl group and a fluorosulfonylhexafluoro-n-propyl group. Of these groups, preferred ones are a fluorine atom, a trifluoromethyl group, a pentafluoroethyl group, a heptafluoro-n-propyl group, a heptafluoro-i-propyl group, a trifluoromethoxy group, a pentafluoroethoxy group, a heptafluoro-n-propoxy group and a heptafluoro-i-propoxy group, far preferred ones are a fluorine atom, a trifluoromethyl group and a trifluoromethoxy group, and the best one is a fluorine atom.

$Rf^3$ and $Rf^4$ each represent a fluorine atom, a perfluorinated monovalent substituent or a perfluorinated divalent substituent independently, $Rf^3$ and $Rf^4$ may combine with each other to form a ring, and each of $Rf^3$, $Rf^4$ and $Rf^5$ may link to form a ring. The monovalent substituent to be perfluorinated may have any of linear, branched and cyclic structures, and the number of carbon atoms contained therein is preferably from 1 to 10, far preferably from 1 to 5, particularly preferably from 1 to 3. Examples of a monovalent substituent to be perfluorinated include an alkyl group (e.g., methyl, ethyl, n-propyl, i-propyl, cyclopropyl), a halogenated alkyl group (e.g., chloromethyl, dichloromethyl, trichloromethyl, 1-chloroethyl, 2-chloroethyl), an alkoxy group (e.g., methoxy, ethoxy, i-propoxy), an acyl group (e.g., formyl, acetyl, propionyl), an acyloxy group (e.g., acetoxy, propionyloxy), an alkoxycarbonyl group (e.g., methoxycarbonyl, ethoxycarbonyl), and a fluorosulfonyl group. Each of these monovalent substituents may further have another substituent.

Examples of a monovalent substituent represented by $Rf^3$ and $Rf^4$ each include a fluorine atom, a trifluoromethyl group, a pentafluoroethyl group, heptafluoro-n-propyl group, heptafluoro-i-propyl group, a chlorodifluoromethyl group, a dichlorofluoromethyl group, a trichloromethyl group, a 1-chlorotetrafluoroethyl group, a 2-chlorotetrafluoroethyl group, a 1,1-dichlorotrifluoroethyl group, a 1,2-dichlorotrifluoroethyl group, a 2,2-dichlorotrifluoroethyl group, a 2,2,2-trichlorodifluoroethyl group, a 1,1,2-trichlorodifluoroethyl group, a 2,2,1-trichlorodifluoroethyl group, a 1,2,2,2-tetrachlorofluoroethyl group, a 1,1,2,2-tetrachloroethyl group, a pentachloroethyl group, a 1-chlorohexafluoro-n-propyl group, a 2-chlorohexafluoro-n-propyl group, a 3-chlorohexafluoro-n-propyl group, a 1-(chlorodifluoromethyl)tetrafluoroethyl group, a 1-(trifluoromethyl)-1-chlorotetrafluoroethyl group, a 1,1-dichloropentafluoro-n-propyl group, a 1,2-dichloropentafluoro-n-propyl group, a 1,3-dichloropentafluoro-n-propyl group, a 2,3-dichloropentafluoro-n-propyl group, a 2,2-dichloropentafluoro-n-propyl group, a 3,3-dichloropentafluoro-n-propyl group, a 1-(chlorodifluoromethyl)-2-chlorotrifluoroethyl group, a 1-(dichlorofluoromethyl)tetrafluoroethyl group, a trifluoromethoxy group, a pentafluoroethoxy group, a heptafluoro-n-propoxy group, a heptafluoro-i-propoxy group, a pentafluoromethoxymethyl group, a heptafluoroethoxymethyl group, a heptafluoromethoxyethyl group, a heptafluoro-1-methoxyethyl group, a trifluoroacetyl group, a pentafluoropropionyl group, a pentafluoroacetylmethyl group, a trifluoromethoxycarbonyl group, a pentafluoroethoxycarbonyl group, a pentafluoromethoxycaronylmethyl group, a trifluoroacetoxy group, a pentafluoroacetoxymethyl group, a pentafluoropropionyloxy group, a fluorosulfonyldifluoromethyl group, a fluorosulfonyltetrafluoroethyl group and a fluorosulfonylhexafluoro-n-propyl group. Of these groups, preferred ones are a fluorine atom, a trifluoromethyl group, a pentafluoroethyl group, a heptafluoro-n-propyl group, a heptafluoro-i-propyl group, a trifluoromethoxy group, a pentafluoroethoxy group, a heptafluoro-n-propoxy group and a heptafluoro-i-propoxy group, far preferred ones are a fluorine atom, a trifluoromethyl group and a trifluoromethoxy group, and the best one is a fluorine atom.

The divalent substituent of $Rf^3$ and $Rf^4$ each may have any of linear, branched and cyclic structures, and the number of carbon atoms contained therein is preferably from 0 to 10, far preferably from 0 to 5, and particularly preferably from 1 to 3. Such a divalent substituent includes an alkylene group and a halogenated alkylene group. The alkylene group and the halogenated alkylene group each may contain an ether linkage. Examples of a divalent substituent represented by $Rf^3$ and $Rf^4$ each include the groups illustrated below, but these examples should not be construed as limiting the scope of the invention.

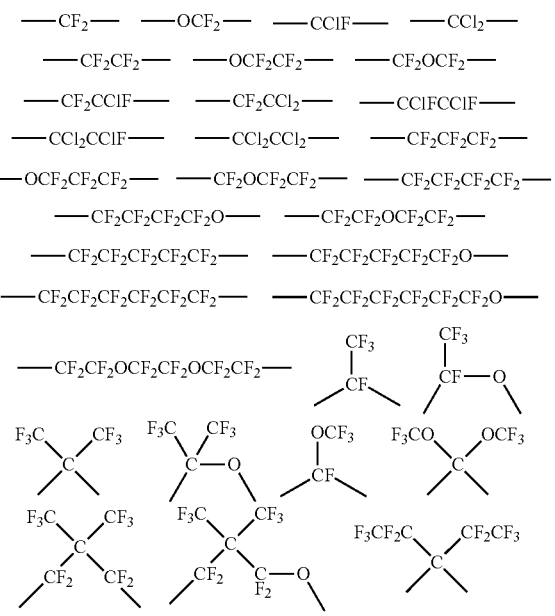

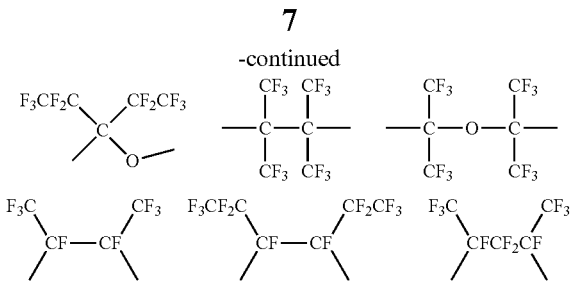

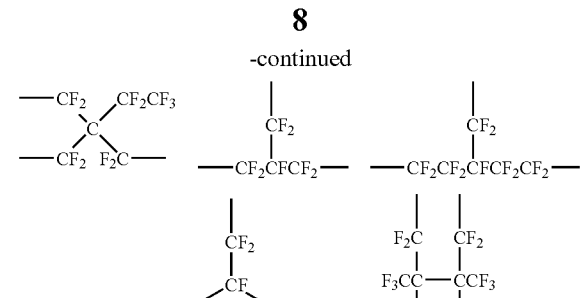

$Rf^5$ represents a perfluorinated (n+1)-valent to (2n+2)-valent linkage group. Herein, n is an integer of 1 to 5. And n is preferably from 1 to 5, far preferably from 1 to 3, further preferably 1 or 2, and particularly preferably 1. The linkage group may have any of linear, branched and cyclic structures, and may contain an ether linkage. The number of carbon atoms contained in the linkage group is preferably from 1 to 15, far preferably from 1 to 10, and particularly preferably from 1 to 6. Moreover, the linkage group may be halogenated.

Examples of $Rf^5$ are illustrated below, but these examples should not be construed as limiting the scope of the invention.

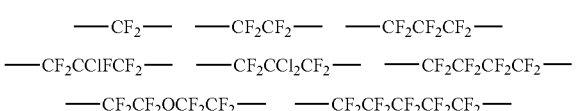
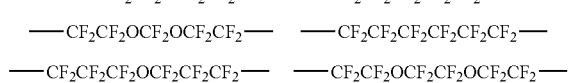
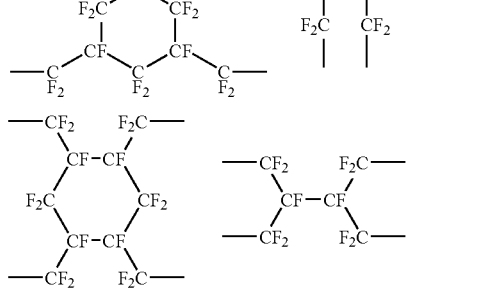
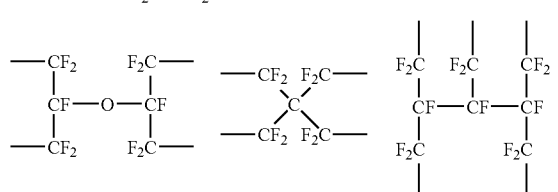
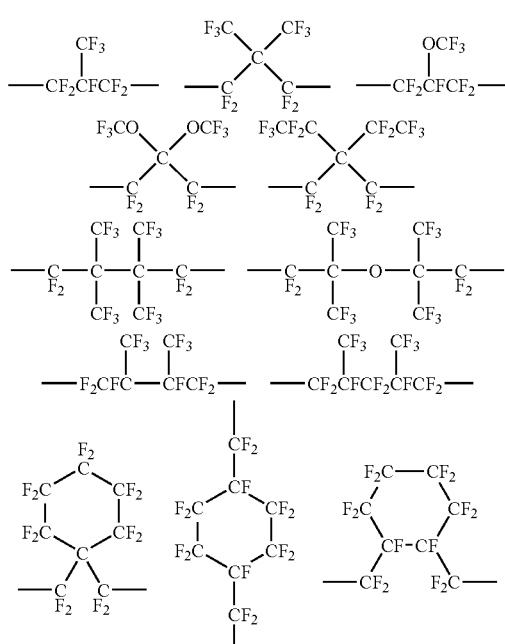
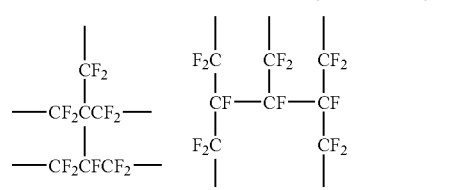
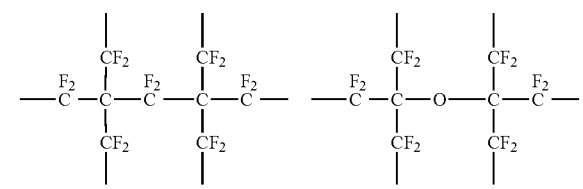
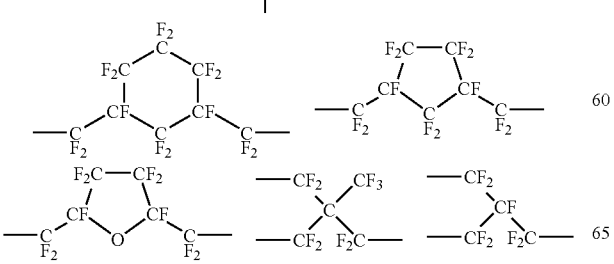
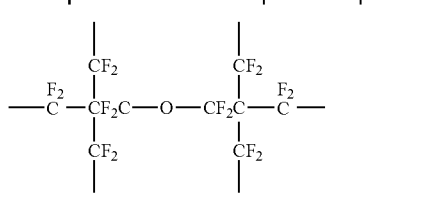

$Rf^6$ represents a perfluorinated tetravalent linkage group. The linkage group may have any of linear, branched and cyclic structures, and may contain an ether linkage. The number of carbon atoms contained in the tetravalent linkage group is preferably from 1 to 20, far preferably from 1 to 15, and particularly preferably from 1 to 10. Moreover, the tetravalent linkage group may be halogenated. Examples of $Rf^6$ are illustrated below, but these examples should not be construed as limiting the scope of the invention.

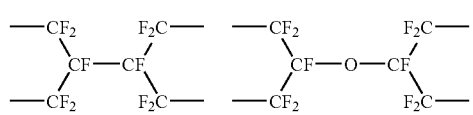

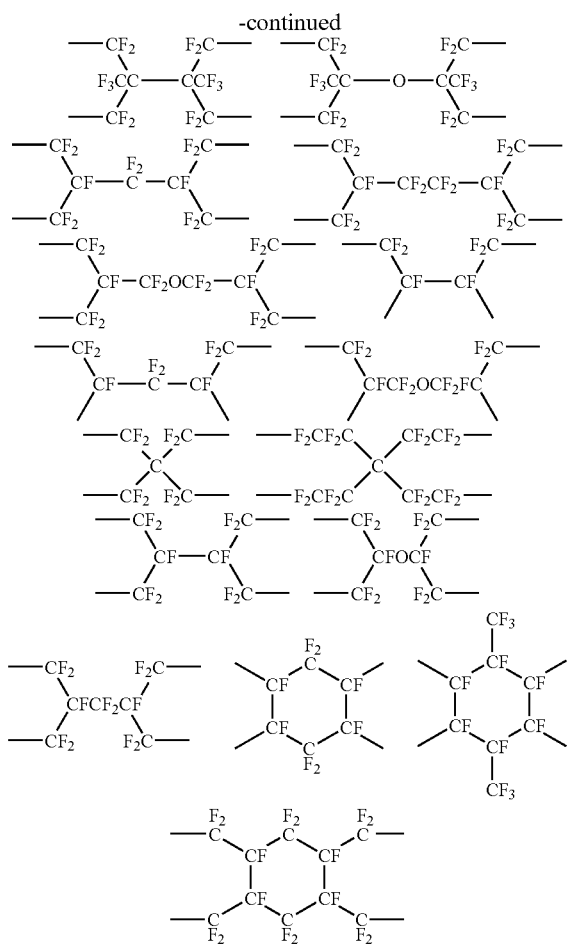

Of compounds represented by the formula (1), the compounds which each have rings formed by combining $Rf^3$ and $Rf^4$ each with $Rf^6$ are preferably compounds represented by the formula (3), and far preferably compounds represented by the formula (5). Of compounds represented by formula (2), the compounds which each have rings formed by combining $Rf^3$ and $Rf^4$ each with $Rf^5$ are preferably compounds represented by the formula (4), and far preferably compounds represented by the formula (6).

The term "thermal decomposition" as used in the invention refers to the reaction that is induced by heating in a compound represented by the formula (1) and yields a compound represented by the formula (2). The thermal decomposition in the invention is carried out in a vapor phase under a reduced pressure. In the thermal decomposition, any of reactors can be used as far as they have shapes allowing efficient heating. For instance, a tubular reactor can be used. When the tubular reactor is used, it is preferred that the reaction be performed with apparatus equipped with a reaction vessel (a vaporizing chamber) for gradually vaporizing a compound having acid fluoride groups (a raw material) and a cold trap for collecting the product of this reaction. The style of thermal decomposition is not particularly restricted, and the thermal decomposition may be carried out in any style. For instance, it is possible to employ the style of continuous reaction wherein an entire raw material is introduced into a vaporizing chamber at a time, or the style of semicontinuous reaction wherein a raw material is divided into portions, and one portion after another is introduced into a vaporizing chamber. In the invention, the thermal decomposition is performed by continuous reaction. The continuous reaction is preferably carried out according to a method of causing a vaporized raw material to flow through a heated reaction tube, obtaining the thus formed perfluorinated polyfunctional olefin compound as an outlet gas, condensing the compound by cooling, and then continuously collecting the condensed matter. The vaporization speed of a compound having acid fluoride groups cannot be confined within specific limits because proper changes are made thereto depending on the reactor's shape and size, the kind of a filler used and the reactivity of the compound. When continuous reaction is carried out at a vaporization speed of 1 to 2 mmol/h by using the same tubular reactor, filler and compounds as in Examples of the invention, the perfluorinated polyfunctional vinyl ether compounds can be obtained in satisfactory yields. In general, vaporization speeds lower than their proper range tend to cause undesirable decomposition reaction of the product, so there is a fear of yield reduction. Vaporization speeds higher than their proper range are also undesirable because they bring about an increase in recovery amount of the unreacted raw material and arouse a fear of lowering the conversion ratio in the reaction.

Vapor-phase thermal decomposition reaction is preferably carried out in a reaction tube in the presence of at least one kind of inorganic solid selected from glass, alkali metal salts or alkaline earth metal salts with the intention of accelerating the reaction. An example of the glass is commonly used soda glass, notably glass beads improved in mobility by having the shape of beads. The alkali metal salts and the alkaline earth metal salts are preferably carbonates or fluorides. Examples of an alkali metal salt include sodium carbonate, potassium carbonate, lithium carbonate, cesium carbonate, potassium fluoride and sodium fluoride. Examples of an alkaline earth metal salts include calcium carbonate, magnesium carbonate, barium carbonate and calcium fluoride. For the purpose of inhibiting formation of hydrogen fluoride adduct, it is preferred that the filler be packed in a reaction tube and dried at a temperature of 200° C. or higher under a reduced pressure for at least 1 hour, preferably at least 3 hours, and then used in the reaction. By this drying operation, formation of hydrogen fluoride adduct is prevented and perfluorinated polyfunctional vinyl ether compounds with high purity can be obtained.

The reaction temperature in the vapor-phase thermal decomposition reaction, though it can be changed as appropriate according to the boiling point and stability of a compound used as a raw material, is preferably from 100° C. to 500° C., far preferably from 150° C. to 300° C. When the reaction temperature is too high, decomposition reaction of the product tends to occur and cause a lowering of yield. On the other hand, too low reaction temperatures are undesirable because of an increase in the amount of the raw material recovered.

The degree of pressure reduction in the vapor-phase thermal decomposition reaction is expressed in absolute pressure. There are no particular restrictions on the measurement method of absolute pressure, and any instrument for measurement of absolute pressure, such as a mercury barometer, a diaphragm gauge, a Pirani gauge or a themistor vacuum gauge, can be used. So, the expression "the degree of pressure reduction is 100 mmHg" means that the degree of pressure reduction is 100 mmHg as expressed in absolute pressure. The method for pressure reduction has no particular restrictions, and the pressure reduction can be performed with a rotary vacuum oil pump, a turbo molecular pump, a diaphragm pump, an aspirator or the like. The thermal decomposition performed under a reduced pressure in the invention can inhibit the occurrence of side-reaction of highly reactive perfluorinated vinyl ether groups, namely decomposition of products, and allows formation of perfluorinated polyfunctional vinyl ether compounds in high yields. Therefore, the degree of pressure reduction in performing the thermal decomposition is preferably 100 mmHg or below, far preferably 50 mmHg or below, from the viewpoint of inhibiting the decomposition of products.

On the ground that an acid fluoride group-containing compound as the raw material undergoes vapor-phase thermal decomposition under a reduced pressure, the boiling point of the compound is preferably 350° C. or below under an absolute pressure of 100 mmHg.

Compounds represented by the formula (1) including those represented by the formula (3), which are substrates of the present vapor-phase thermal decomposition reaction, are not particularly restricted as to ways to get them, and can be manufactured by heretofore known methods. For instance, the compounds corresponding to the case of n=1 among compounds represented by the formula (1), notably the compound (8) illustrated hereinafter, can be manufactured according to the method disclosed in U.S. Pat. No. 3,250,807, brochure. More specifically, compounds corresponding to the case of n=1 among compounds represented by the formula (1), as illustrated in the following reaction scheme, can be manufactured by addition of hexafluoropropylene oxide (HFPO) to compounds having two —COF groups (provided that $Rf^7$ in the following formulae represents a divalent perfluorinated substituent). According to this manufacturing method, compounds corresponding to the case of n=2 in the formula (1) can be manufactured from compounds having three —COF groups, and compounds corresponding to the case of n=3 in the formula (1) from compounds having four —COF groups.

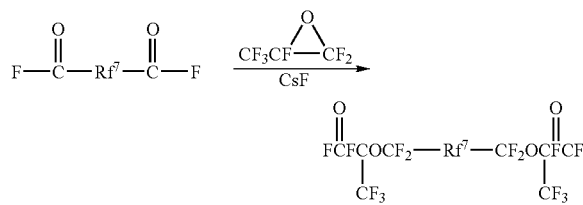

The compounds having three —COF groups can be manufactured according to the method described, e.g., in JP-A-61-18071. More specifically, they can be manufactured, as illustrated below, by subjecting compounds each having three —COCl groups to electrolytic fluorination and making NaF act thereon (provided that $R^8$ represents a trivalent substituent and Re represents the perfluorinated $R^8$ in the following formulae).

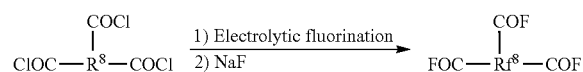

Compounds having four —COF groups can be manufactured by the method as described, e.g., in JP-A-1-226844. More specifically, as illustrated in the following reaction scheme, they can be manufactured by allowing compounds each having two —COF groups to react with an epoxy compound, and further allowing SbF$_5$ to act on the reaction products (provided that $Rf^9$ in the following formulae represents a divalent perfluorinated substituent).

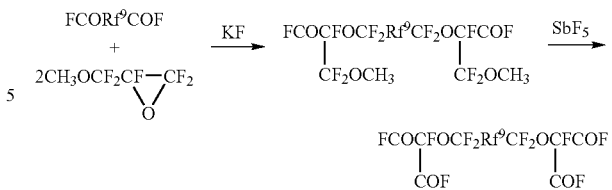

Compounds represented by the formula (3) including those represented by the formula (5) can be manufactured by the method described, e.g., in JP-A-2007-13165. More specifically, as shown in the following reaction scheme, they can be manufactured by forming spiro-compounds by condensation reaction between tetraol $R^6(OH)_4$ and fluorine-containing ketone compounds, subjecting the spiro-compounds to liquid-phase fluorination, and allowing NaF to act thereon (provided that $R^6$ in the following formula represents a tetravalent linkage group to be converted into $Rf^6$ by perfluorination).

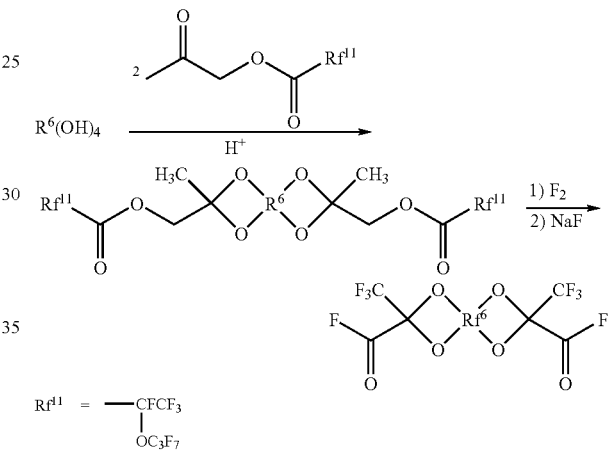

In accordance with the invention, compounds each having a plurality of acid fluoride groups are thermally decomposed under a reduced pressure, and the decomposition products thus formed can escape undergoing further decomposition. Thus, perfluorinated polyfractional vinyl ether compounds can be obtained in high yields. In other words, side-reaction of the perfluorinated vinyl ether groups can be inhibited. In the invention, the number of perfluorinated vinyl ether groups in the product has no particular limits, and perfluorinated polyfunctional vinyl ether compounds which each have two or more perfluorinated vinyl ether groups can be manufactured. On the other hand, $Rf^1$, $Rf^2$, $Rf^3$, $Rf^4$, $Rf^5$ and $Rf^6$ in compounds represented by the formulae (1), (2), (3) and (4) are groups stable at temperatures for the performance of thermal decomposition and have no significant effects on reactivity to thermal decomposition. In addition, compounds represented by the formula (1) including those represented by the formula (3) can be obtained with ease according to the manufacturing method as mentioned above. Thus, the invention is not limited to the manufacturing method for Compound (6) and Compound (9) illustrated hereinafter, but can be applied to the manufacturing of compounds represented by the formula (2) from those represented by the formula (1), notably compounds represented by the formula (4) from those represented by the formula (3).

EXAMPLES

Examples for illustrating the invention in the concrete are given below, but the invention should not construed as being limited to these examples. Herein, nuclear magnetic resonance spectrometry is abbreviated to NMR, and gas chromatography mass spectroscopy is abbreviated to GC-MS. In $^{19}$F-NMR, measurements were made using fluorotrichloromethane as an external standard.

Example 1

Manufacturing of Perfluorinated Divinyl Ether (6)

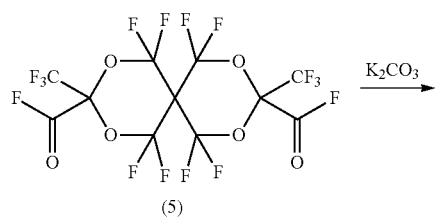

(5)

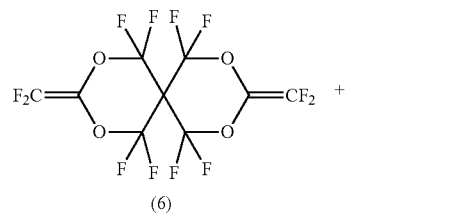

(6)

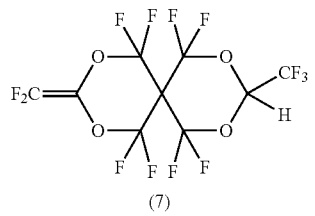

(7)

A glass columnar reaction tube (inside diameter: 14 mm, length: 340 mm) was filled with 6 g of potassium carbonate. To one end of the reaction tube, a 10 mL of eggplant-type flask (vaporizing chamber) for sample injection was connected, and to the other end of the reaction tube, a cold trap was connected. Further, the cold trap was connected to a vacuum pump via an alkali trap. The pressure inside the apparatus in its entirety was reduced to 4 mmHg, and the reaction tube was heated up to temperatures ranging from 203° C. to 206° C. by means of a tubular furnace, and under these conditions the filler was dried for 6 hours. Then, a perfluorinated diacid fluoride, specifically Compound (5), in an amount of 930 mg (1.75 mmol) was injected into the vaporizing chamber, and the vaporizing chamber was heated from 35° C. up to 83° C. over 75 minutes on an oil bath, thereby vaporizing Compound (5). The reaction product was condensed with the trap cooled to −78° C., and collected. After conclusion of the vaporization, collection of the product was further continued for 30 minutes. The degree of pressure reduction during the reaction was from 6 to 16 mmHg. A product collection accumulated in the cold trap was analyzed by $^{19}$F-NMR, and thereby it was found that Compound (6) was obtained in an amount of 569.7 mg (1.42 mmol, yield: 81.5 mole %). And the Compound (7) content in Compound (6) was 0.43 mole %.

$^{19}$F-NMR of Compound (6) [CDCl$_3$1]: δ [ppm]=−70.7 (s, 8F, —CF$_2$—), −111.3 (s, 4F, =CF$_2$); GC-MS [SEI, 70 eV]: m/z=400 [M]$^+$.

Example 2

Manufacturing of Perfluorinated Divinyl Ether (6)

Manufacturing of Compound (6) was carried out in the same manner as in Example 1, except that Compound (5) was vaporized by controlling the degree of pressure reduction during the reaction to a range of 47 to 54 mmHg and heating the vaporizing chamber from 40° C. up to 90° C. over 75 minutes on the oil bath. A product collection accumulated in the cold trap was analyzed by $^{19}$F-NMR, and thereby it was found that Compound (6) was obtained in an amount of 504 mg (1.26 mmol, yield: 72.1 mole %). And the Compound (7) content in Compound (6) was 0.44 mole %.

Example 3

Manufacturing of Perfluorinated Divinyl Ether (6)

Manufacturing of Compound (6) was carried out in the same manner as in Example 1, except that Compound (5) was vaporized by controlling the degree of pressure reduction during the reaction to a range of 82 to 97 mmHg and heating the vaporizing chamber from 45° C. up to 100° C. over 75 minutes on the oil bath. A product collection accumulated in the cold trap was analyzed by $^{19}$F-NMR, and thereby it was found that Compound (6) was obtained in an amount of 442 mg (1.10 mmol, yield: 63.2 mole %). And the Compound (7) content in Compound (6) was 0.49 mole %.

Comparative Example 1

Manufacturing of Perfluorinated Divinyl Ether (6)

A glass columnar reaction tube (inside diameter: 14 mm, length: 340 mm) was filled with 6 g of potassium carbonate, and the same apparatus as used in Example 1 was structured. The pressure inside the apparatus in its entirety was reduced to 4 mmHg, and the reaction tube was heated up to temperatures ranging from 203° C. to 206° C. by means of a tubular furnace, and under these conditions the filler was dried for 6 hours. Then, nitrogen gas was introduced into the apparatus until the pressure inside the apparatus in its entirety reached to normal atmospheric pressure. Thereafter, a perfluorinated diacid fluoride, specifically Compound (5), in an amount of 930 mg (1.75 mmol) was injected into the vaporizing chamber. And Compound (5) was vaporized by heating the vaporizing chamber from 50° C. up to 150° C. over 75 minutes on the oil bath while blowing nitrogen gas into the vaporizing chamber with a flow rate of 10 ml/min, thereby performing the reaction in a stream of nitrogen under normal atmospheric pressure. A product collection accumulated in the cold trap was analyzed by $^{19}$F-NMR, and thereby it was found that Compound (6) was obtained in an amount of 174 mg (0.435 mmol, yield: 24.9 mole %). And the Compound (7) content in Compound (6) was 0.52 mole %.

Example 4

Manufacturing of Perfluorinated Divinyl Ether (9)

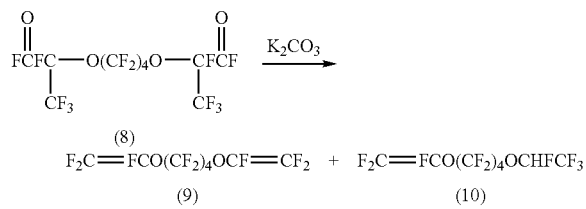

A glass columnar reaction tube (inside diameter: 14 mm, length: 340 mm) was filled with 6 g of potassium carbonate, and the same apparatus as used in Example 1 was structured. The pressure inside the apparatus in its entirety was reduced to 4 mmHg, and the reaction tube was heated up to temperatures ranging from 203° C. to 206° C. by means of a tubular furnace, and under these conditions the filler was dried for 4 hours. Then, a perfluorinated diacid fluoride, specifically Compound (8), in an amount of 920 mg (1.75 mmol) was injected into the vaporizing chamber, and the vaporizing chamber was heated from 35° C. up to 70° C. over 70 minutes on an oil bath, thereby vaporizing Compound (8). After conclusion of the vaporization, collection of the product was further continued for 30 minutes. The degree of pressure reduction during the reaction was from 5 to 14 mmHg. A product collection accumulated in the cold trap was analyzed by $^{19}$F-NMR, and thereby it was found that Compound (9) was obtained in an amount of 566.2 mg (1.44 mmol, yield: 82.1 mole %). And the Compound (10) content in Compound (9) was 0.39 mole %.

$^{19}$F-NMR of Compound (9) [CDCl$_3$]: δ [ppm]=−86.40 (m, 4F), −115.05 (dd, J=69.6, 90.9 Hz, 2F), −123.19 (dddd, J=5.7, 6.3, 90.9, 119.1 Hz, 2F), −126.77 (m, 4F), −137.62 (dddd, J=6.2, 6.3, 69.9, 118.8 Hz, 2 F).

According to the invention, perfluorinated compounds including perfluorinated polyfunctional vinyl ether compounds can be manufactured in high yields. The perfluorinated polyfunctional vinyl ether compounds obtained in the invention have exceedingly low hydrogen fluoride adduct contents, and they are very useful as raw materials of fluoropolymers.

The entire disclosure of each and every foreign patent application from which the benefit of foreign priority has been claimed in the present application is incorporated herein by reference, as if fully set forth.

What is claimed is:

1. A method of manufacturing a compound represented by formula (2), the method comprising:
   thermally decomposing a compound represented by formula (1) by a flow method under a reduced pressure:

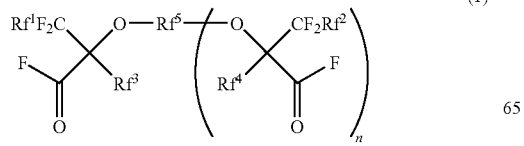

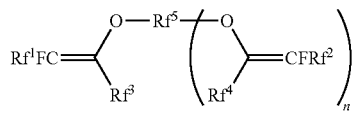

wherein Rf$^1$ and Rf$^2$ each independently represents a fluorine atom or a perfluorinated monovalent substituent;
Rf$^3$ and Rf$^4$ each independently represents a fluorine atom, a perfluorinated monovalent substituent or a perfluorinated divalent substituent;
Rf$^3$ and Rf$^4$ may combine with each other to form a ring;
each of Rf$^3$ and Rf$^4$ may combine with Rf$^5$ to form a ring; and
Rf$^5$ represents a perfluorinated (n+1)-valent to (2n+2)-valent linkage group, provided that n represents an integer of 1 to 5.

2. The manufacturing method according to claim 1, wherein the compound represented by formula (1) is thermally decomposed under an absolute pressure of 100 mmHg or below.

3. The manufacturing method according to claim 1, wherein the compound represented by formula (1) is thermally decomposed under an absolute pressure of 50 mmHg or below.

4. The manufacturing method according to claim 1, wherein the compound represented by formula (1) has a boiling point of 350° C. or below under an absolute pressure of 100 mmHg.

5. The manufacturing method according to claim 1, wherein the compound represented by formula (1) is a compound represented by formula (3) and the compound represented by formula (2) is a compound represented by formula (4):

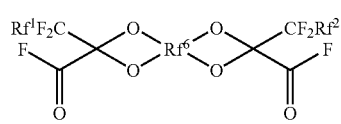

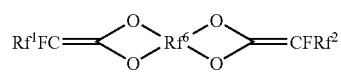

wherein Rf$^1$ and Rf$^2$ each independently represents a fluorine atom or a perfluorinated monovalent substituent; and
Rf$^6$ represents a perfluorinated tetravalent linkage group.

6. The manufacturing method according to claim 5, wherein the compound represented by formula (3) is a compound represented by formula (5); and
the compound represented by formula (4) is a compound represented by formula (6):

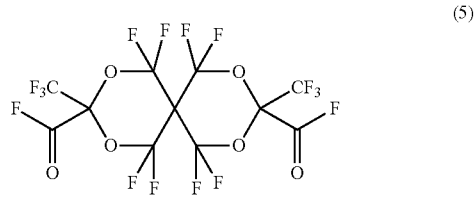

-continued
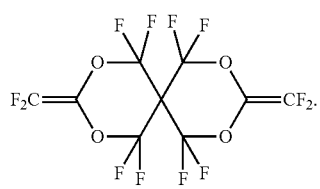
(6)
7. The manufacturing method according to claim 1, wherein the compound represented by formula (1) is thermally decomposed at a reaction temperature of from 100° C. to 500° C.
8. The manufacturing method according to claim 1, wherein the compound represented by formula (1) is thermally decomposed at a reaction temperature of from 150° C. to 300° C.
* * * * *